United States Patent

Ohta et al.

Patent Number: 4,977,175
Date of Patent: Dec. 11, 1990

[54] 4,5,6,7-TETRAHYDROBENZIMIDAZOLE DERIVATIVES AS 5HT$_3$-ANTAGONISTS

[75] Inventors: Mitsuaki Ohta; Tokuo Koide; Takeshi Suzuki; Akira Matsuhisa, all of Ibaraki; Isao Yanagisawa; Keiji Miyata, both of Tokyo, all of Japan

[73] Assignee: Yamanouchi Pharmaceutical Co., Ltd., Tokyo, Japan

[21] Appl. No.: 450,748

[22] Filed: Dec. 14, 1989

[30] Foreign Application Priority Data

Dec. 22, 1988 [JP] Japan ................................. 63-325327
Feb. 28, 1989 [JP] Japan ..................................... 1-48896

[51] Int. Cl.$^5$ .................. A61K 31/415; C07D 235/04
[52] U.S. Cl. ..................................... 514/394; 548/325
[58] Field of Search .......................... 548/325; 514/394

[56] References Cited

U.S. PATENT DOCUMENTS 4,826,990 5/1989 Musset et al. ........................ 548/235

Primary Examiner—Mary C. Lee
Assistant Examiner—Robert C. Whittenbaugh
Attorney, Agent, or Firm—Burgess, Ryan & Wayne

[57] ABSTRACT

4,5,6,7-Tetrahydrobenzimidazole derivatives represented by general formula (I)

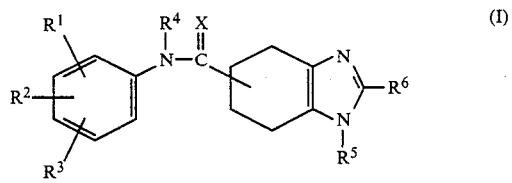

wherein groups represents the following:

$R^1$, $R^2$, $R^3$: independently represent hydrogen atom, hydroxy group, a halogen atom, a lower alkyl group which may optionally be substituted with a halogen atom, a lower alkoxy group, a lower alkylthio group, an aralkyloxy group, an aryloxy group, a lower alkanoyl group, carboxy group, a lower alkoxycarbonyl group or nitro group;

$R^4$, $R^5$, $R^6$: hydrogen atom or a lower alkyl group;

X: oxygen atom or sulfur atom;

or salts thereof which are believed to have a 5-HT$_3$ antagonizing activity.

10 Claims, No Drawings

4,5,6,7-TETRAHYDROBENZIMIDAZOLE DERIVATIVES AS 5HT₃-ANTAGONISTS

BACKGROUND OF THE INVENTION

Field of the Invention

The present invention relates to 4,5,6,7-tetrahydrobenzimidazole derivatives represented by general formula (I) described below or salts thereof which are useful as drugs:

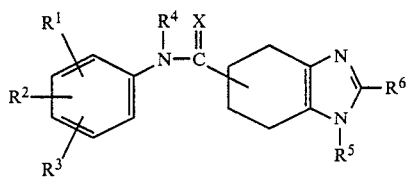

(wherein groups represents the following:
$R^1$, $R^2$, $R^3$: independently represent hydrogen atom, hydroxy group, a halogen atom, a lower alkyl group which may optionally be substituted with a halogen atom, a lower alkoxy group, a lower alkylthio group, an aralkyloxy group, an aryloxy group, a lower alkanoyl group, carboxy group, a lower alkoxycarbonyl group or nitro group;
$R^4$, $R^5$, $R^6$: hydrogen atom or a lower alkyl group;
X : oxygen atom or sulfur atom; hereafter the same).

DESCRIPTION OF THE PREFERRED EMBODIMENTS

In the definitions for the groups in the general formula in the present specification, the term "lower" refers to a straight or branched carbon chain having 1 to 6 carbon atoms, unless otherwise indicated.

Accordingly, the "lower alkyl group" includes methyl group, ethyl group, propyl group, butyl group, pentyl group, hexyl group, isopropyl group, isobutyl group, tert-butyl group, isopentyl group, tert-pentyl group, isohexyl group, etc.

The "lower alkoxy group" includes methoxy group, ethoxy group, propoxy group, butoxy group, pentyloxy group, hexyloxy group, isopropoxy group, isobutoxy group, tert-butoxy group, isopentyloxy group, tert-pentyloxy group, isohexyloxy group, 2-ethylbutoxy group, etc. The "lower alkylthio group" includes methylthio group, ethylthio group, propylthio group, butylthio group, pentylthio group, isopropylthio group, isobutylthio group, tert-butylthio group, isopentylthio group, etc. The "lower alkanoyl group" includes formyl group, acetyl group, propionyl group, butyryl group, isobutyryl group, valeryl group, etc. The "lower alkoxycarbonyl group" includes methoxycarbonyl group, ethoxycarbonyl group, propoxycarbonyl group, isopropoxycarbonyl group, butoxycarbonyl group, tert-butoxycarbonyl group, pentyloxycarbonyl group, hexyloxycarbonyl group, etc.

Furthermore the "aryloxy group" includes phenyloxy group, naphthyloxy group, etc. The "aralkyloxy group" includes benzyloxy group, phenethyloxy group, phenylpropoxy group, phenylbutoxy group, etc. The "halogen atom" includes fluorine atom, chlorine atom, bromine atom and iodine atom.

The compounds of the present invention can form salts thereof. Examples of such salts are salts with inorganic acids such as hydrochloric acid, hydrobromic acid, boric acid, phosphoric acid, sulfuric acid, etc.; and salts with organic acids such as acetic acid, tartaric acid, dibenzoyl tartaric acid, maleic acid, fumaric acid, citric acid, succinic acid, benzoic acid, p-toluenesulfonic acid, etc.

Furthermore, the compounds of the present invention contain asymmetric carbons and the compounds falling under general formula (I) include all isomers such as optically active isomers, racemic isomers and the like, based on these asymmetric carbons.

PROCESSES

Hereafter processes of producing the compounds of the present invention are specifically described below.

PROCESS (I):

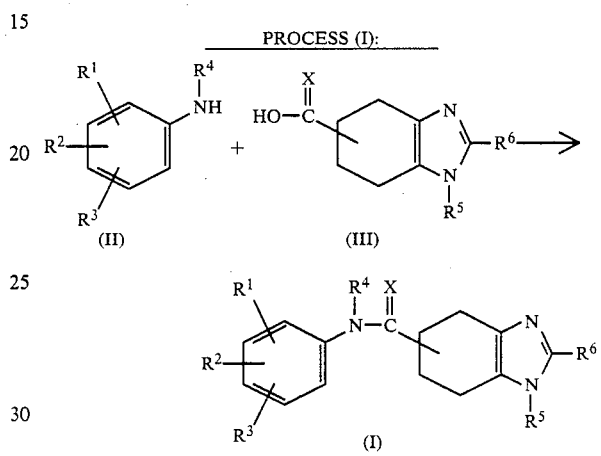

Compound (I) of the present invention can be obtained by reacting an aniline derivative represented by general formula (II) with a 4,5,6,7-tetrahydrobenzimidazole -5-carboxylic acid (or thiocarboxylic acid) represented by general formula (III) or reactive derivatives thereof.

The reaction between Compound (II) and Compound (III) or reactive derivatives thereof can be carried out generally in a solvent at room temperature or with heating. Any solvent is usable without particular limitation so long as it does not take part in the reaction. Examples of the solvent which is generally used include acetone, dioxan, ether, tetrahydrofuran, methyl ethyl ketone, chloroform, dichloroethane, dichloromethane, ethyl acetate, ethyl formate, dimethylformamide, dimethylsulfoxide, etc. These solvents may also be used by appropriately mixing them.

Compound (III) may be used in a free carboxylic acid and in addition thereto, may also be provided for the reaction as reactive derivatives of carboxylic acid. As the reactive derivatives of carboxylic acid, an activated ester (e.g., 1-hydroxy benzotriazole ester, etc.), a mixed acid anhydride, an acid halide, an activated amide, an acid anhydride, an acid azide, etc. can be used. When Compound (III) is used in the form of free carboxylic acid, it is preferred to use a condensing agent such as N,N'-dicyclohexylcarbodiimide, N,N'-diethylcarbodiimide, etc.

Depending upon kind of the reactive derivatives of carboxylic acid, it is sometimes advantageous to conduct the reaction in the presence of bases, from such a standpoint that the reaction proceeds smoothly. Examples of such bases include inorganic bases such as sodium hydrogencarbonate, potassium hydrogencarbonate, sodium carbonate, potassium carbonate, etc.; organic bases such as trimethylamine, triethylamine, dimethylaniline, pyridine, etc.

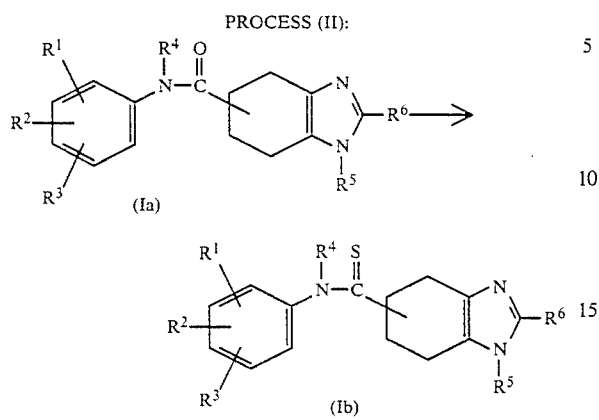

The process is directed to production of 4,5,6,7-tetrahydrobenzimidazole-5-thiocarboxamide derivatives represented by general fomula (Ib).

That is, the carboxamide derivatives represented by general formula (Ia) are reacted with phosphorus pentasulfide or Lawesson's reagent in a solvent such as benzene, toluene, xylene, tetrahydrofuran, dioxan, etc. The reaction temperature is room temperature or under reflux with heating.

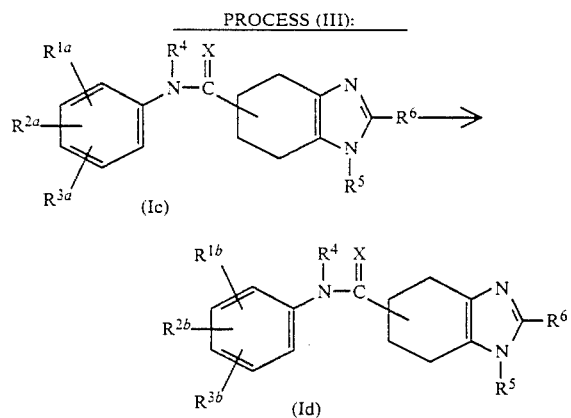

[wherein $R^{1a}$, $R^{2a}$ and $R^{3a}$ independently represent hydrogen atom, hydroxy group, a halogen atom, a lower alkyl group which may optionally be substitued with a halogen atom, a lower alkoxy group, a lower alkylthio group, an aralkyloxy group, a lower alkanoyl group, carboxy group or a lower alkoxycarbonyl group; $R^{1b}$, $R^{2b}$ and $R^{3b}$ independently represent hydrogen atom, hydroxy group, a halogen atom, a lower alkyl group which may optionally be substituted with a halogen atom, a lower alkoxy group, a lower alkylthio group, a lower alkanoyl group, carboxy group or a lower alkoxycarbonyl group; with proviso that at least one of $R^{1a}$, $R^{2a}$ and $R^{3a}$ is a protected hydroxy group (e.g., benzyloxy group, trimethylsilyloxy group or acetoxy group) and at least one of $R^{1b}$, $R^{2b}$ and $R^{3b}$ is hydroxy group].

The process is directed to preparation of compounds containing hydroxy groups which are represented by general formula (Id).

That is, the compounds can be prepared by subjecting compounds represented by general formula (Ic) to ordinary catalytic hydrogenation in the presence of a catalyst such as platinum, palladium, Raney nickel, rhodium, etc.

PROCESS (IV):

Furthermore, the compounds of the present invention can also be obtained by alkylating the compounds represented by general formula (Ie).

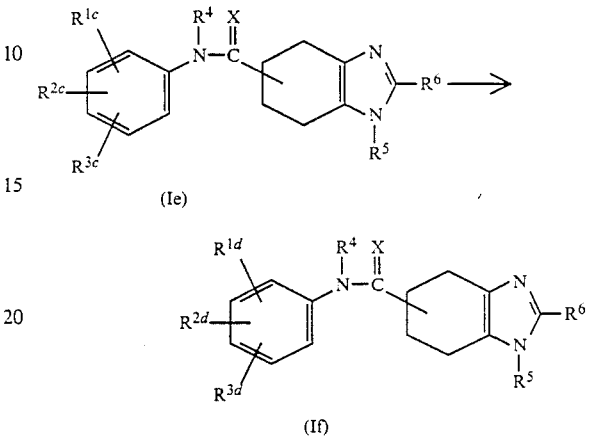

[wherein $R^{1c}$, $R^{2c}$ and $R^{3c}$ independently represent hydrogen atom, hydroxy group, a halogen atom, a lower alkyl group which may optionally be substituted with a halogen atom, a lower alkoxy group, a lower alkylthio group, an aralkyloxy group, a lower alkanoyl group, carboxy group or a lower alkoxycarbonyl group, (with proviso that at least one of $R^{1c}$, $R^{2c}$ and $R^{3c}$ is hydroxy group); and $R^{1d}$, $R^{2d}$ and $R^{3d}$ independently represent hydrogen atom, hydroxy group, a halogen atom, a lower alkyl group which may optionally be substituted with a halogen atom, a lower alkoxy group, a lower alkylthio group, a lower alkanoyl group, carboxy group or a lower alkoxycarbonyl group, (with proviso that at least one of $R^{1d}$, $R^{2d}$ and $R^{3d}$ is a lower alkoxy group)].

Appropriate alkylation can be adopted from a method which comprises reacting with a lower alcohol such as methanol, ethanol, propanol, etc. in the presence of a dehydrating agent such as hydrochloric acid, sulfuric acid, an aromatic sulfonic acid, etc.; a method which comprises reacting a halogenated lower alkyl such as methyl iodide, ethyl iodide, propyl iodide, etc. in the presence of a base such as sodium carbonate, potassium carbonate, etc.; a method which comprises reacting with an alkyl sulfate such as diethyl sulfate, etc. in the presence of an alkali, and the like, taking reaction conditions into account.

The reaction solvent may be a solvent inert to the reaction, such as water, an alcohol, e.g., methanol, ethanol, etc., acetone, tetrahydrofuran, ether, dioxan, chloroform, dichloromethane, etc. Alternatively, the reaction may also be conducted in the absence of any solvent.

The thus prepared compounds of the present invention are isolated and purified in the free form as they are or in the form of salts thereof. The isolation and purification can be performed by applying ordinary chemical operations such as extraction, crystallization, recrystallization, various chromatographies, etc.

The racemic compounds can be led to stereochemically pure isomers by using appropriate starting compounds or by conventional racemic resolution [for example, by a method which comprises leading to a diastereomer with an ordinary optically active acid (tartaric acid, etc.) followed by optical resolution, etc.].

EFFECTS OF THE INVENTION

The compounds of the present invention or its salts thereof specifically inhibited transient bradycardia induced by serotonin in anesthesized rat and are thus believed to have a 5-HT$_3$-antagonizing activity. Therefore, the compounds of the present invention prevent vomiting induced by anticancer agents such as Cisplatin or the like and radiation and are considered to be effective in the prophylaxis and treatment of migraine, cluster headache, trigeminal neuralgia, anxiety, gastrointestinal disorders, peptic ulcer, irritable bowel syndrome, etc.

As 5-HT$_3$ antagonists, there are heretofore known azabicyclo compounds described in GB 2125398, GB 2166726, GB 2166727 and GB 2126728 (Japanese Pat. Application Laid-Open Nos. 59-36675 and 59-67284); tetrahydrocarbazole compounds described in GB 2153821 (Japanese Pat. Application Laid-Open No. 60-214784); azabicyclo compounds described in EP 200444 (Japanese Pat. Application Laid-Open No. 61-275276), etc. However, the compounds of the present invention are potent 5-HT$_3$ antagonists which have the structure totally different from the compounds described above.

The pharmacological effects of the compounds according to the present invention were confirmed as follows.

(1) 5-HT$_3$-antagonizing activity

Wistar strain male rats of 9 week age were anesthesized with intraperitoneally administering 1 g/kg of urethane. Under artificial respiration, blood pressure and heart rate were measured. Transient reduction in heart rate and in blood pressure induced by intravenous administration of serotonin or 2-methylserotonin which is a selective agonist of 5-HT$_3$ was used as an index for the reaction via 5-HT$_3$ receptor (Bezold-Jarisch reflex : Paintal, A.S., Physiol. Rev., 53, 159, 1973).

The compounds of the present invention or salts thereof were intravenously administered (0.03 to 3 μg/kg) 10 minutes before or orally administered (1 to 30 μg/kg) 60 minutes before the administration of serotonin and 2-methylserotonin, the reduction in heart rate and blood pressure induced by serotonin or 2-methylserotonin was dose-dependently inhibited.

Inhibitory activity of the compounds of the present invention on serotonin-induced Bezold-Jarisch (BJ) reflex in rats is shown in the table below.

| BJ Reflex Inhibitory Activity (ED$_{50}$; μg/kg) | | |
| --- | --- | --- |
| Example | i.v. | p.o. |
| 1 | 0.32 | 5.9 |
| 13 | 1.2 | 6.6 |

(2) Cancerocidal agent-induced vomiting inhibitory action

By administering the compounds of the present invention subcutaneously or orally to male ferret weighing 1 to 1.5 kg in a dose of 0.01 to 0.3 mg/kg, vomiting induced by intraperitoneal administration of 10 mg/kg of Cisplatin was prevented.

(3) Stress defecation inhibitory action

Wistar strain male rats of 9 week age were encased in a cage for restricted stress and the number of feces was measured. The compounds of the present invention or salts thereof dose-dependently prevented acceleration of defecation induced by restricted stress.

The compounds of the present invention have low toxicity. Acute toxicity in male mice (up and down method) was 100 to 150 mg/kg i.v.

A pharmaceutical composition comprising at least one of the compounds of the present invention or salts thereof is prepared into the form of tablets, powders, granules, capsules, pills, liquids, injections, suppositories, ointments, pastes, etc. using carriers, excipients and other additives conventionally used for pharmaceutical compositions. The composition may be administered orally (including sublingual administration) or parenterally.

As the carrier or excipient for pharmaceutical composition, there are solid or liquid non-toxic pharmaceutical substances. Examples include lactose, magnesium stearate, starch, talc, gelatin, agar, pectin, gum arabic, olive oil, sesame oil, cocoa butter, ethylene glycol, etc. and other materials conventionally used.

A clinical dose of the compound of the present invention is appropriately determined, taking into account conditions, body weight, age, sex, etc. of the patient applied, but a daily dose will normally be 0.1 to 10 mg for intravenous administration and 0.5 to 50 mg for oral administration, for adult. The dose may be administered once or more than once a day.

EXAMPLES

Hereafter the present invention is described in more detail by referring to the examples. Processes for preparing starting compounds used in the examples are shown in Reference Examples below.

REFERENCE EXAMPLE 1

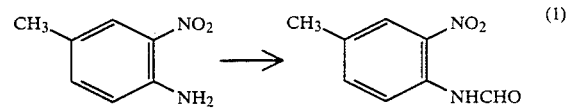

(1)

4-Methyl-2-nitroaniline, 30 g (197 mmols), was dissolved in 500 ml of methylene chloride and a liquid mixture of 52 ml (1.378 mol) of formic acid and 31 ml (328 mmols) of acetic anhydride was added dropwise to the solution. The mixture was stirred at room temperature for 16 hours. The solvent was distilled off under reduced pressure. The resulting crystals were washed with ether to give 34.7 g (97.7%) of N-(4-methyl-2-nitrophenyl)formamide.

Physicochemical properties:
NMR (DMSO-d$_6$, TMS, 100 MHz):
δ 2.40 (3H, s, CH$_3$), 7.55 (1H, dd, 10Hz, 1Hz, ArH), 7.90 (2H, bs, ArH), 8.40 (1H, bs, CHO), 10.40 (1H, br, NH).
Mass spectrum (EI):m/z 180 (M+).

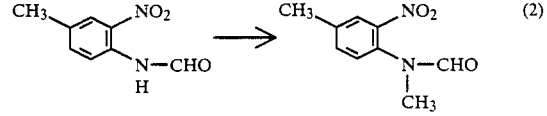

(2)

In an argon flow, 8.1 g (202 mmols) of sodium hydride (60% in oil) was added to 400 ml of dry dimethylformamide and the mixture was cooled to 5° to 10° C. To the mixture was dropwise added 34.7 g (192 mmols) of N-(4-methyl -2nitrophenyl)formamide (a solution in 150 ml of dry dimethylformamide). The mixture was stirred at 50° C. for an hour. After cooling again to 5° to 10° C., 18 ml (289 mmols) of methyl iodide (a solution in 30 ml of dry dimethylformamide) was dropwise added to the mixture. The system was stirred at room temperature for 16 hours. After the solvent was distilled off under reduced pressure, 200 ml of water was added to the residue followed by extraction with ethyl acetate. After the ethyl acetate layer was washed with saturated aqueous sodium chloride solution and dried over anhydrous magnesium sulfate, the solvent was distilled off under reduced pressure. The resulting crystals were washed with n-hexane to give 31.2 g (83.4%) of N-methyl-N-(4-methyl2-nitrophenyl)formamide.

Physicochemical properties:
NMR (DMSO-d$_6$, TMS, 100 MHz):
δ 2.44 (3H, d, 1Hz, CH$_3$), 3.10, 3.40 (3H, s, N-CH$_3$), 7.60 (2H, m, ArH), 7.90 (1H, d, 14Hz, ArH), 8.18 (1H, d, 8Hz CHO).
Mass spectrum (FAB, Pos): m/z 195 (M$^+$+1).

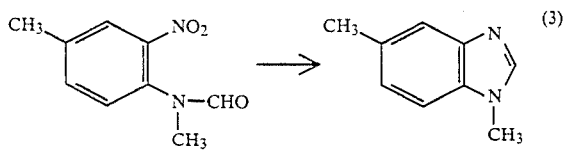

N-Methyl-N-(4-methyl-2-nitrophenyl)formamide, 20 g (103 mmols), was added to 400 ml of ethanol and a solution of sodium hydrosulfite, 54g (310 mmols) in 300ml of water was added dropwise to the mixture at 80° C. After stirring at 80° C. for 7 hours, the mixture was stirred at room temperature for further 16 hours. The solvent was distilled off under reduced pressure and 200 ml of 1N sodium hydroxide aqueous solution was added to the residue followed by extraction with ethyl acetate. The organic layer was dried over anhydrous magnesium sulfate and evaporated. The resulting crystals were washed with ether to give 10.0 g (67,3%) of 1,5-dimethylbenzimidazole.

Physicochemcial properties:
NMR (DMSO-d$_6$, TMS, 100 MHz): δ 2.44 (3H, s, CH$_3$), 3.82 (3H, s, N-Me), 7.10 (1H, dd, 8Hz, 1Hz, ArH), 7.45 (2H, m, ArH), 8.10 (1H, s, 2-H).
Mass spectrum (EI):m/z 146 (M$^+$).

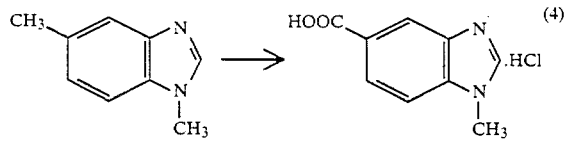

1,5-Dimethylbenzimidazole, 8.5 g (58.1 mmols), was added to 250 ml of water and 21 g (133 mmols) of potassium permanganate was added portionwise to the mixture at 50° to 60° C. The mixture was stirred for 2 hours at the same temperature. After cooling, the mixture was filtered and 1 N hydrochloric acid was added to the filtrate to render pH 4. Distillation under reduced pressure gave 20.2 g (including inorganic matters) of 1-methylbenzimidazole-5- carboxylic acid hydrochloride.

Physicochemical properties:
NMR (CD$_3$OD, TMS, 100 MHz): δ 4.20 (3H, s, N-Me), 8.05 (1H, dd, 10Hz, 1Hz, ArH), 8.35 (1H, dd, 10Hz, ArH), 8.50 (1H, q, 1Hz, ArH), 9.54 (1H, s, 2-H).
Mass spectrum (FAB, Pos):m/z 177 (M$^{30}$ +1, as a free base).

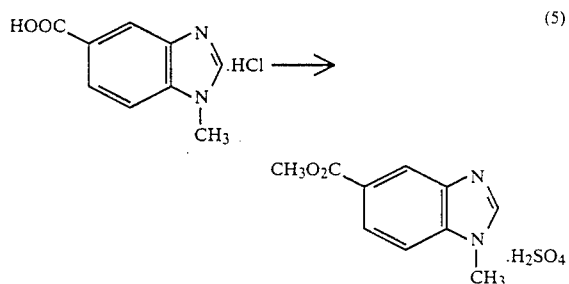

1-Methylbenzimidazole-5-carboxylic acid hydrochloride, 20.2 g (including inorganic matters), was added to 300 ml of methanol and 5 ml of conc. hydrochloric acid was added to the mixture followed by heating to reflux for 7 hours. The solvent was distilled off and 200 ml of water was added to the residue. At 5° to 10° C., 1 N sodium hydroxide solution was added to the mixture to adjust pH to 9 to 10 followed by extraction with ethyl acetate. The ethyl acetate layer was dried over anhydrous magnesium sulfate and filtered. The solvent was distilled off under reduced pressure. The resulting crystals were washed with ether to give 4.8 g of methyl 1-methyl-benzimidazole-5-carboxylate (43.6%, based on 1,5-dimethylbenzimidazole).

Physicochemical properties:
NMR (DMSO-d$_6$, TMS, 90 MHz): δ 3.86 (6H, s, N-Me, CO$_2$Me), 7.65 (1H, dd, 10Hz, 1Hz, ArH), 7.94 (1H, dd, 10Hz, 1Hz, ArH), 8.24 (1H, d, 1Hz, ArH), 8.32 (1H, s, 2-H)
Mass spectrum (EI):m/z 190 (M$^+$).

The above-described compound, 4.8 g, was dissolved in 26.6 ml of 2 N sulfuric acid and the solvent was distilled off under reduced pressure to give 7.2 g of methyl 1-methylbenzimidazole-5-carboxylate sulfate.

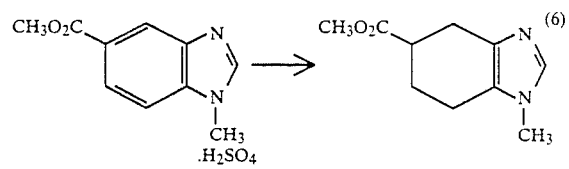

In an autoclave 6.6 g (22.9 mmols) of methyl 1-methylbenzimidazole-5-carboxylate sulfate, 60 ml of acetic acid and 3.0 g of 5% rhodium-carbon powders were charged and hydrogenation was carried out at 80° C. for 92 hours under 60 atms. After cooling, rhodium-carbon powders were filtered off and the filtrate was distilled off under reduced pressure. After 200 ml of water was added to the residue, 1 N sodium hydroxide solution was added to the mixture at 0° to 5° C. to adjust pH to 9 to 10 followed by extraction with ethyl acetate. The ethyl acetate layer was dried over anhydrous magnesium sulfate and the solvent was distilled off to give 3.45 g (77.7%) of methyl 1-methyl-4,5,6,7-tetrahydrobenzimid-azole-5-carboxylate (oil).

Physicochemical properties:

NMR (CDCl$_3$, TMS, 100 MHz): δ 1.70–3.00 (7H, m, CH$_2$×3, CH), 3.50 (3H, s, N-CH$_3$), 3.70 (3H, s, CO$_2$CH$_3$), 7.30 (1H, s, 2-H).

Mass spectrum (EI):m/z 194 (M+).

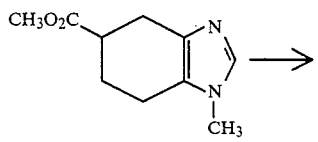

(7)

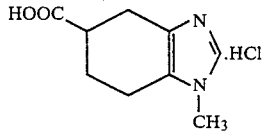

After 3.45 g (17.7 mmols) of methyl 1-methyl-4,5,6,7-tetrahydrobenzimidazole-5-carboxylate was added to 130 ml of methanol, 3.53 g (88.3 mmols) of sodium hydroxide (15 ml of water) was added to the mixture followed by heating to reflux for 5 hours. The solvent was distilled off under reduced pressure and 100 ml of 1 N hydrochloric acid was added to the residue. The mixture was distilled off under reduced pressure to give 8.5 g (including 57 w/w % of NaCl) of 1-methyl-4,5,6,7-tetrahydrobenzimidazole-5-carboxylic acid hydrochloride.

Physicochemical properties:

NMR (CD$_3$OD, TMS, 60 MHz): δ 2.00–3.10 (7H, m, CH$_2$×3, CH), 3.80 (3H, s, N-CH$_3$), 8.75 (1H, s, 2-H).

Mass spectrum (EI):m/z 180 (M+, as a free base).

REFERENCE EXAMPLE 2

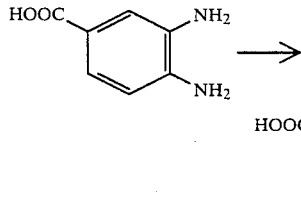

(1)

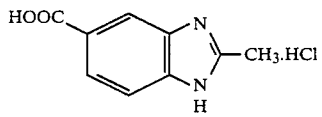

After a mixture of 5.0 g (32.8 mmols) of 3,4-diaminobenzoic acid, 50 ml of conc. hydrochloric acid and 10 ml (0.175 mol) of acetic acid was heated at 100° C. for 24 hours, the solvent was distilled off under reduced pressure to give 6.6 g (94.5%) of 2-methylbenzimidazole-5-carboxylic acid hydrochloride.

Physicochemical properties:

NMR (DMSO-d$_6$, TMS, 90 MHz): δ 2.85 (3H, s, 2-CH$_3$), 7.84 (1H, dd, 8Hz, 1Hz, ArH), 8.05 (1H, dd, 8Hz, 1Hz, ArH), 8.24 (1H, d, 1Hz, ArH).

Mass spectrum (FAB, Pos): m/z 177 (M++1, as a free base).

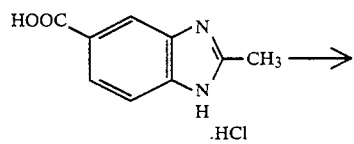

(2)

-continued

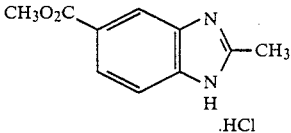

2-Methylbenzimidazole-5-carboxylic acid hydrochloride, 6.6 g (32.5 mmols), was added to 200 ml of methanol and 5 ml of conc. hydrochloric acid was added to the mixture followed by heating to reflux for 8 hours. The solvent was distilled off under reduced pressure and 200 ml of water was added to the residue. After 1 N sodium hydroxide solution was added to the mixture to adjust pH to 9 to 10, the mixture was extracted with ethyl acetate. The ethyl acetate layer was dried over anhydrous magnesium sulfate and filtered. The solvent was distilled off to give 5.5 g (93.2%) of methyl 2-methyl-benzimidazole-5-carboxylate.

Physicochemical properties:

NMR (CDCl$_3$, TMS, 60 MHz): δ 2.65 (3H, s, 2-CH$_3$), 3.90 (3H, s, OCH$_3$), 7.65 (2H, ABq, J=8Hz, Δγ=21Hz, ArH), 8.20 (1H, s, ArH).

Mass spectrum (FAB, Pos):m/z 191 (M++1).

The above-described compound, 5.7 g, was dissolved in 30 ml of 1 N hydrochloric acid and the solvent was distilled off under reduced pressure to give 6.8 g of methyl 2-methylbenzimidazole-5-carboxylate hydrochloride.

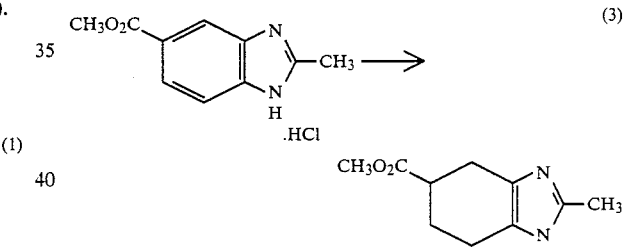

(3)

In an autoclave 6.8 g (30 mmols) of methyl 2-methyl-benzimidazole-5-carboxylate hydrochloride, 6.0 g of 5% palladium-barium sulfate and 140 ml of acetic acid were charged and hydrogenation was carried out at 80° C. for 115 hours under 60 atms with stirring. After cooling, 5% palladium-barium sulfate was filtered off and the filtrate was distilled off under reduced pressure. After 200 ml of water was added to the residue, 1 N sodium hydroxide solution was added to the mixture at 0° to 5° C. to adjust pH to 9 to 10 followed by extraction with ethyl acetate. The ethyl acetate layer was dried over anhydrous magnesium sulfate and the solvent was distilled off under reduced pressure. The residue was subjected to silica gel column chromatography and eluted with methylene chloride-methanol (10 : 1) to give 0.70 g (12.0%) of methyl 2-methyl-4,5,6,7-tetrahydrobenzimidazole-5-carboxylate.

Physicochemical properties:

NMR (CDCl$_3$, TMS, 60 MHz): δ 1.80–3.00 (7H, m, CH$_2$×3, CH), 2.35 (3H, s, 2-CH$_3$), 3.70 (3H, s, OCH$_3$), 9.90 (1H, s, NH).

Mass spectrum (FAB, Pos):m/z 195 (M++1).

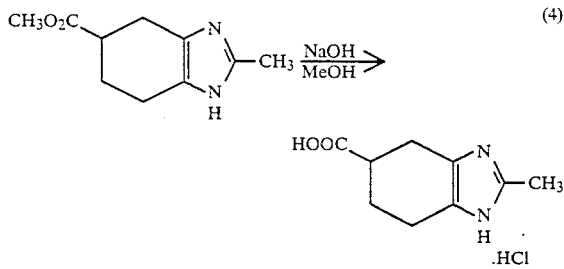

After 0.70 g (3.6 mmols) of methyl 2-methyl 4,5,6,7-tetrahydrobenzimidazole-5-carboxylate was added to 40 ml of methanol, a solution of 0.74 g (18.5 mmols) of sodium hydroxide in 2 ml of H₂O was added to the mixture followed by heating to reflux for 16 hours. After the solvent was distilled off under reduced pressure, 100 ml of 1 N hydrochloric acid was added to the residue. The mixture was distilled off under reduced pressure to give 1.6 g (including 58 w/w % of NaCl) of 2-methyl-4,5,6,7-tetrahydrobenzimidazole-5-carboxylic acid hydrochloride.

Physicochemical properties:
NMR (CD₃OD, TMS, 60 MHz): δ 2.00–3.00 (7H, m, CH₂,CH), 2.60 (3H, s, 2-CH₃).
Mass spectrum (EI):m/z 180 (M⁺, as a free base).

EXAMPLE 1

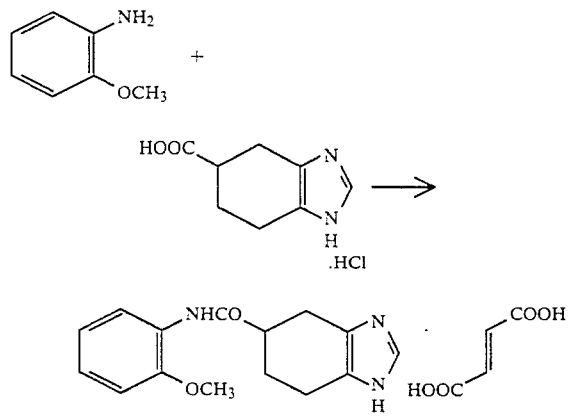

After 0.60 g (2.95 mmols) of 4,5,6,7-tetrahydrobenzimidazole-5-carboxamide acid hydrochloride was added to 5 ml of thionyl chloride, the mixture was heated at 90° C. for 2.5 hours. After thioayl chloride was distilled off under reduced pressure, 10 ml of dichloromethane, 0.4 ml (3.57 mmols) of o-anisidine and 1.0 ml (7.22 mmols) of thriethylamine were added to the residue followed by stirring at room temperature for 18 hours. After the mixture was washed with 5% aqueous sodium hydrogencarbonate solution and then dried over anyhdrous magnesium sulfate, the solvent was distilled off under reduced pressure. The residual oil was purified by silica gel column chromatography (eluant: dichloromethane : methanol =10 : 1). To 0.22 g of the resulting foamy substance was added 0.10 g of fumaric acid ethanol to form the fumarate. The fumarate was recyrstallized from ethyl acetate-methanol (10 : 1) to give N-(2-methyloxyphenyl) -4,5,6,7-tetrahydrobenzimidazole-5carboxamide fumarate 0.8hydrate.

Physicochemical properties:
Melting point: 168–170° C.

| Elemental analysis (as C₁₀H₂₁H₃O₆.0.8H₂O) | | | |
|---|---|---|---|
| | C (%) | H (%) | N (%) |
| Calcd. | 56.79 | 5.67 | 10.46 |
| Found | 56.91 | 5.62 | 10.42 |

NMR (CDCl₃): δ (ppm) 2.20 (2H, br, CH₂), 2.90 (5H, m, CH₂×2, CH), 3.84 (3H, s, OCH₃), 6.90 (3H, m, H of aromatic ring), 7.50 (1H, br, 2-CH), 7.96 (1H, s, CONH), 8.35 (1H, dd, 9Hz, H of aromatic ring).
Mass spectrum (EI):m/z 271 (M⁺, as a free base).

EXAMPLE 2

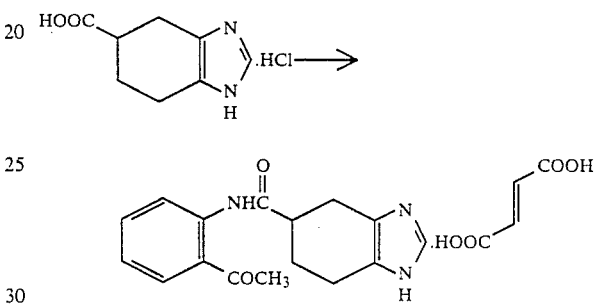

After 0.13 g of 4,5,6,7-tetrahydrobenzimidazole -5-carboxylic acid hydrochloride (containing sodium chloride) was refluxed in 0.7 ml of thionyl chloride for 30 minutes, volatile components were distilled off under reduced pressure. The resulting residue was added to a solution of 0.14 g of 2-aminoacetophenone and 0.15 ml of triethylamine in 2 ml of dichloromethane under ice cooling. After the mixture was stirred at room temperature overnight, 5 ml of an aqueous sodium carbonate solution was added to the mixture followed by extraction with chloroform. The organic phase was dried over anhydrous magnesium sulfate and the solvent was distilled off under reduced pressure. The residue was then subjected to column chromatography (silica gel, chloroform-methanol to give 0.14 g of N-(2-acetylphenyl)-4,5,6,7-tetrahydrobenzimidazole-5-carboxamide. By treating the base with a fumaric acid solution in methanol-acetonitrile, 0.15 g of N-(2-acetylphenyl)-4,5,6,7-tetrahydrobenzimidazole-5-carbox amide fumarate was obtained.

Physicochemical properties:
Melting point: 94°–98° C.

| Elemental analysis (as C₁₆H₁₇N₃O₂.0.5H₂O.0.5CH₃CN) | | | |
|---|---|---|---|
| | C (%) | H (%) | N (%) |
| Calcd. | 58.80 | 5.52 | 11.43 |
| Found | 58.81 | 5.38 | 11.43 |

Mass spectrum (EI):m/z 283 (M⁺, as a free base).
The following compounds were obtained in a similar manner to Example 2.

EXAMPLE 3

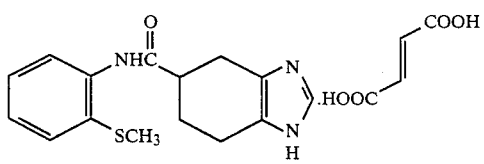

N-(2-Methylthiophenyl)-4,5,6,7-tetrahydrobenzimidazole-5-carboxamide fumarate

Physicochemical properties:
Melting point: 143°–145° C. (methanol-acetonitrile).

| Elemental analysis (as $C_{15}H_{17}N_3OS \cdot C_4H_4O_4 \cdot 0.2H_2O \cdot 0.15CH_3CN$) | | | | |
|---|---|---|---|---|
| | C (%) | H (%) | N (%) | S (%) |
| Calcd. | 56.10 | 5.33 | 10.68 | 7.76 |
| Found | 56.12 | 5.28 | 10.50 | 7.77 |

Mass spectrum (EI):m/z 287 ($M^+$, as a free base).

EXAMPLE 4

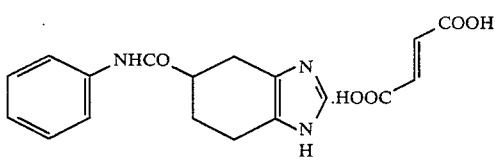

N-Phenyl-4,5,6,7-tetrahydrobenzimidazole-5-carboxamide fumarate

Physicochemical properties:
Melting point: 186°–188° C.

| Elemental analysis (as $C_{14}H_{15}N_3O \cdot \frac{3}{4}C_4H_4O_4 \cdot 0.7H_2O$) | | | |
|---|---|---|---|
| | C (%) | H (%) | N (%) |
| Calcd. | 59.88 | 5.73 | 12.32 |
| Found | 59.89 | 5.58 | 12.26 |

Mass spectrum (FAB, POS):m/z 242 ($M^+ + 1$, as a free base).

EXAMPLE 5

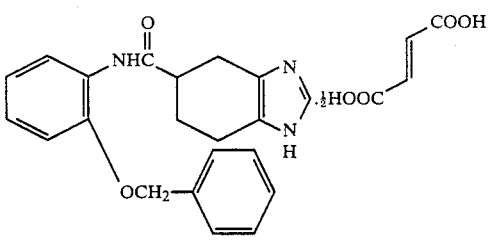

N-(2-Benzyloxyphenyl)-4,5,6,7-tetrahydrobenzimidazole-5-carboxamide 0.5 fumarate Physicochemical properties:
Melting point: 199°–201° C. (methanol-acetonitrile).

| Elemental analysis (as $C_{21}H_{21}N_3O_2 \cdot 0.5C_4H_4O_4$) | | | |
|---|---|---|---|
| | C (%) | H (%) | N (%) |
| Calcd. | 68.13 | 5.72 | 10.36 |
| Found | 68.18 | 5.83 | 10.36 |

Mass spectrum (EI):m/z 347 ($M^+$, as a free base).

EXAMPLE 6

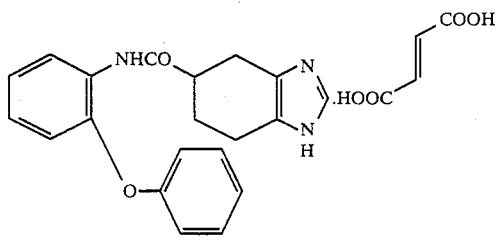

N-(2-Phenoxyphenyl)-4,5,6,7-tetrahydrobenzimidazole-5-carboxamide fumarate

Physicochemical properties:
Melting point: 182°–183° C. (methanol-acetonitrile).

| Elemental analysis (as $C_{20}H_{19}N_3O_2 \cdot C_4H_4O_4 \cdot 0.2H_2O$) | | | |
|---|---|---|---|
| | C (%) | H (%) | N (%) |
| Calcd. | 63.63 | 5.21 | 9.27 |
| Found | 63.70 | 5.24 | 9.23 |

Mass spectrum (EI):m/z 333 ($M^+$, as a free base).

EXAMPLE 7

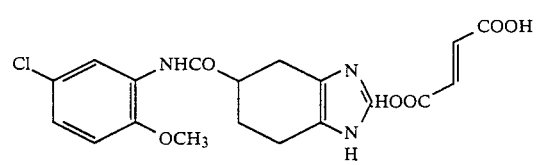

N-(3-Chloro-6methoxyphenyl)-4,5,6,7-tetrahydrobenzimidazole-5carboxamide fumarate Physicochemical properties:
Melting point: 149°–152° C. (methanol-acetonitrile).

| Elemental analysis (as $C_{15}H_{16}ClN_3O_2 \cdot C_4H_4O_4 \cdot 0.7H_2O$) | | | | |
|---|---|---|---|---|
| | C (%) | H (%) | Cl (%) | N (%) |
| Calcd. | 52.53 | 4.96 | 8.16 | 9.62 |
| Found | 52.49 | 4.98 | 8.32 | 9.67 |

Mass spectrum (EI):m/z 305, 307 ($M^+$, as a free base).

EXAMPLE 8

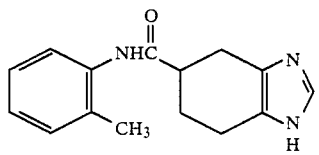

N-(2-Methylphenyl)-4,5,6,7-tetrahydrobenzimidazole-5-carboxamide

Physicochemical properties:
Melting point: 100°–105° C. (ethyl acetate).
MNMR (CDCl$_3$-CD$_3$OD-TMS): δ ppm 2.00–3.00 (7H, m, CH$_2$ and CH), 2.25 (3H, s, Me), 7.10–7.50 (5H, m, ArH)
Mass spectrum (EI):m/z 255 (M$^{30}$).

EXAMPLE 9

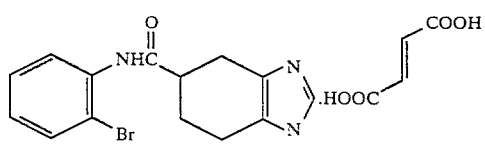

N-(2-Bromophenyl)-4,5,6,7-tetrahydrobenzimidazole-5-carboxamide fumarate

Physicochemical properties:
Melting point: 98°–100° C. (ethyl acetate-methanol).

| Elemental analysis (as C$_{14}$H$_{14}$BrN$_3$O.C$_4$H$_4$O$_4$) | | | | |
|---|---|---|---|---|
| | C (%) | H (%) | N (%) | Br (%) |
| Calcd. | 49.55 | 4.15 | 9.63 | 18.31 |
| Found | 49.27 | 4.02 | 9.44 | 18.55 |

Mass spectrum (FAB):m/z 320, 322 (M$^+$ +1, as a free base).

EXAMPLE 10

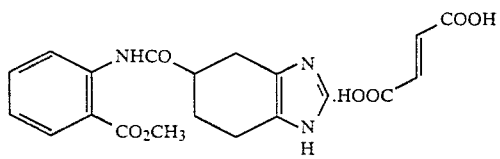

N-(2-Methoxycarbonylphenyl)-4,5,6,7-tetrahydrobenzimidazole-5-carboxamide fumarate Physicochemical properties:
Melting point: 95°–97° C. (ethyl acetate-methanol).

| Elemental analysis (as C$_{16}$H$_{17}$N$_3$O$_2$.C$_4$H$_4$O$_4$) | | | |
|---|---|---|---|
| | C (%) | H (%) | N (%) |
| Calcd. | 57.59 | 5.63 | 11.19 |
| Found | 57.30 | 5.23 | 11.00 |

Mass spectrum (FAB):m/z 300 (M+1, as a free base).

EXAMPLE 11

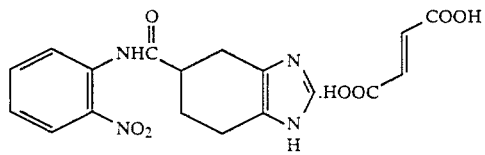

N-(2-Nitrophenyl)-4,5,6,7-tetrahydrobenzimidazole-5-carboxamide fumarate.

Physicochemical properties:
Melting point: 144°–146° C. (ethyl acetate-methanol)

| Elemental analysis (as C$_{14}$H$_{14}$N$_4$O$_3$.C$_4$H$_4$O$_4$) | | | |
|---|---|---|---|
| | C (%) | H (%) | N (%) |
| Calcd. | 53.73 | 4.50 | 13.92 |
| Found | 53.89 | 4.30 | 13.71 |

Mass spectrum (FAB):m/z : 287 (M$^+$ +1, as a free base).

EXAMPLE 12

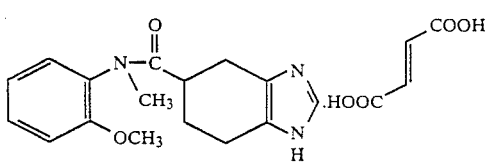

N-(2-Methoxyphenyl)-N-methyl-4,5,6,7tetraphydrobenzimidazole-5-carboxamide fumarate Physicochemical properties:
Melting point: 124°–127° C. (methanol-acetonitrile).

| Elemental analysis (as C$_{16}$H$_{19}$N$_3$O$_2$.C$_4$H$_4$O$_4$.0.7H$_2$O) | | | |
|---|---|---|---|
| | C (%) | H (%) | N (%) |
| Calcd. | 58.02 | 5.94 | 10.15 |
| Found | 57.89 | 5.66 | 9.87 |

Mass spectrum (EI):m/z 286 (M$^+$ +1, as a free base).

EXAMPLE 13

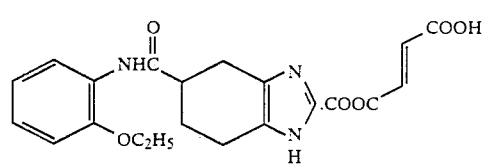

N-(2-Ethoxyphenyl)-4,5,6,7-tetrahydrobenzimidazole-5-carboxamide fumarate

Physicochemical properties:
Melting point: 89°–92° C. (ethyl acetate-methanol).

| Elemental analysis (as C$_{16}$H$_{19}$N$_3$O$_2$.C$_4$H$_4$O$_4$) | | | |
|---|---|---|---|
| | C (%) | H (%) | N (%) |
| Calcd. | 59.84 | 5.77 | 10.46 |
| Found | 59.55 | 5.74 | 10.33 |

Mass spectrum (FAB):m/z 286 (M$^+$, as a free base).

EXAMPLE 14

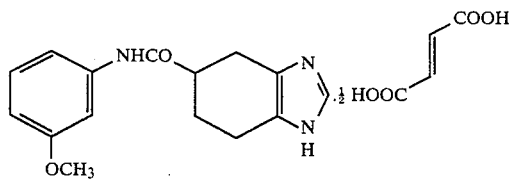

N-(3-Methyoxyphenyl)-4,5,6,7-tetrahydrobenzimidazole-5-carboxamide 0.5 fumarate

Physicochemical properties:
Melting point: 195°–196° C. (methanol-acetonitrile).

| Elemental analysis (as $C_{15}H_{17}N_3O_2.0.5C_4H_4O_4$) | | | |
|---|---|---|---|
| | C (%) | H (%) | N (%) |
| Calcd. | 62.00 | 5.81 | 12.76 |
| Found | 61.87 | 5.85 | 12.46 |

Mass spectrum (EI):m/z 271 (M+, as a free base).

EXAMPLE 15

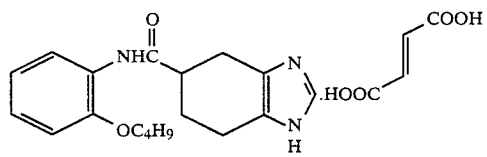

(N-(2-Butyloxyphenyl)-b 4,5,6,7-tetrahydrobenzimidazole-5-carboxamide fumarate

Physicochemical properties:
Melting point: 157°–160° C. (methanol-acetonitrile).

| Elemental analysis (as $C_{18}H_{23}N_3O_2.C_4H_4O_4.0.4H_2O$) | | | |
|---|---|---|---|
| | C (%) | H (%) | N (%) |
| Calcd. | 60.51 | 6.42 | 9.62 |
| Found | 60.21 | 6.10 | 9.71 |

Mass spectrum (EI):m/z 313 (M+, as a free base).

EXAMPLE 16

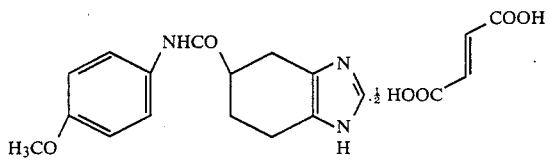

N-(4-Methoxyphenyl)-4,5,6,7-tetrahydrobenzimidazole-5-carboxamide 0.5 fumarate

Physicochemical properties:
Melting point: 217°14 218° C. (methanol-acetonitrile).

| Elemental analysis (as $C_{17}H_{19}N_3O_4.0.2H_2O$) | | | |
|---|---|---|---|
| | C (%) | H (%) | N (%) |
| Calcd. | 61.33 | 5.87 | 12.62 |

| -continued | | | |
|---|---|---|---|
| Elemental analysis (as $C_{17}H_{19}N_3O_4.0.2H_2O$) | | | |
| | C (%) | H (%) | N (%) |
| Found | 61.28 | 5.84 | 12.61 |

Mass spectrum (EI):m/z 271 (M+, as a free base).

EXAMPLE 17

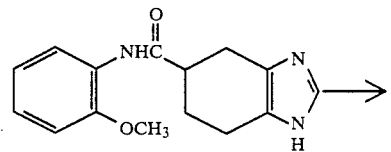

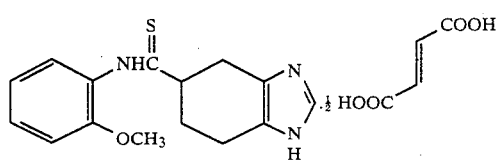

N-(2-Methoxyphenyl)-4,5,6,7-tetrahydrobenzimidazole-5-carboxamide, 0.24 g (0.88 mmol), obtained in Example 1 was added to 10 ml of toluene and 0.36 g (0.89 mmol) of Lawesson's reagent was further added thereto followed by heating at 110°to 120° C. for 16 hours. After cooling, toluene was distilled off and 20 ml of water was added to the residue. To the mixture was added 1 N sodium hydroxide solution to render alkaline. The mixture was extracted with chloroform. After the chloroform phase was dried over anhydrous magnesium sulfate and filtered, the filtrate was distilled off under reduced pressure. The residue was separated and purified by silica gel column chromatography. After 0.08 g (0.69 mmol) of fumaric acid was added to 0.20 g of the resulting foamy substance to convert into the fumarate, the fumrate was recyrstallized from ethyl acetate-methanol (10 : 1) to give 0.12 g (34.3%) of N-(2-methoxyphenyl)-4,5,6,7-tetrahydrobenzimidazole-5-thiocarboxamide ½ fumarate.

Physicochemical properties:
Melting point: 218°–219° C.

| Elemental analysis (as $C_{15}H_{17}N_3OS.\frac{1}{2}C_4H_4O_4$) | | | | |
|---|---|---|---|---|
| | C (%) | H (%) | N (%) | S (%) |
| Calcd. | 59.11 | 5.54 | 12.16 | 9.28 |
| Found | 58.91 | 5.46 | 12.01 | 9.68 |

Mass spectrum (FAB, Pos):m/z 288 (M++1, as a free base).

EXAMPLE 18

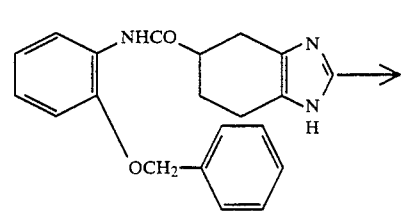

-continued

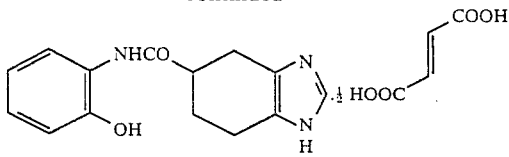

N-(2-Benzyloxyphenyl)-4,5,6,7-tetrahydrobenzimidazole-5-carboxdamide (0.24 g) was catalytically hydrogenated in a solution of ethanol (15 ml) under normal pressure using 30 mg of 10% palladium carbon as a catalyst. After the catalyst was filtered off, the reaction solution was concentrated and the residue was subjected to silica gel column chromatography (3 g). Elution with 10% methanol-chloroform gave 0.10 g (56%) of N-(2-hydroxyphenyl)-4,5,6,7-tetrahydrobenzimidazole-5-carbo xamide, a part of which was purified in the form of the fumarate.

Physicochemical properties:
Melting point: 203°-205° C. (methanol-acetonitrile).

| Elemental analysis (as $C_{14}H_{15}N_3O_2.0.5C_4H_4O_4.0.5H_2O$) | | | |
|---|---|---|---|
| | C (%) | H (%) | N (%) |
| Calcd. | 59.25 | 5.59 | 12.96 |
| Found | 59.21 | 5.32 | 12.90 |

Mass spectrum (EI):m/z 257 (M+, as a free base).

EXAMPLE 19

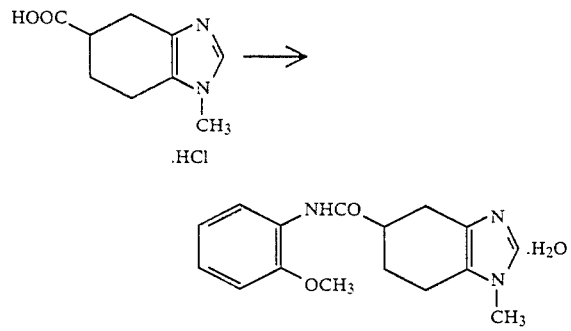

Thionyl chloride, 10 ml, was added to 1.4 g (2.7 mmols) of 1-methyl-4,5,6,7-tetrahydrobenzimidazole-5-carboxylic acid hydrochloride (including NaCl) obtained in Reference Example 1 and the mixture was heated at 90° C. for 4 hours. After thionyl chloride was distilled off under reduced pressure, 10 ml of dichloromethane was added to the residue and at 0° to 4° C., 0.50 ml (4.4 mmols) of o-anisidine and 1.0 ml (7.2 mmols) of triethylamine were added to the mixture followed by stirring at room temperature for 21 hours. After 40 ml of dichloromethane was added to the reaction mixture, the mixture was washed with 1 N sodium hydroxide solution and then dried over anhydrous magnesium sulfate, the solvent was distilled off. The residue was subjected to silica gel column chromatography and eluted with dichloromethane methanol-ammonia water (10 : 1 : 0.1). The solvent was distilled off and the resulting crystals were recyrstallized from ethyl acetate to give 0.18 g of N-(2-methyoxyphenyl)-4,5,6,7-tetrahydrobenzimidazole -5-carboxamide hydrate.

Physicochemical properties:
Melting point: 94°-96° C.

| Elemental analysis (as $C_{16}H_{19}N_3O_2.H_2O$) | | | |
|---|---|---|---|
| | C (%) | H (%) | N (%) |
| Calcd. | 63.34 | 6.97 | 13.85 |
| Found | 63.02 | 6.92 | 13.74 |

Mass spectrum (EI):m/z 285 (M+).

EXAMPLE 20

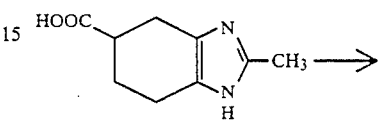

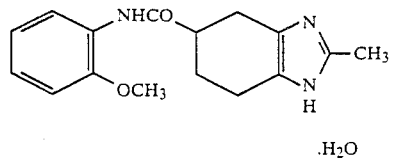

Thionyl chloride, 5 ml, was added to 0.50 g (0.97 mmols) of 2-methyl-4,5,6,7-tetrahydrobenzimidazole-5carboxylic acid hydrochloride (including 58 w/w % of NaCl) obtained in Reference Example 2 and the mixture was heated at 90° C. for 3 hours. After thionyl chloride was distilled off under reduced pressure, 10 ml of methylene chloride was added to the residue and at 0° to 5° C., 0.20 ml (1.78 mmol) of o-anisidine and 0.40 ml (2.89 mmols) of triethylamine were added to the mixture followed by stirring at room temperature for 16 hours. After 50 ml of methylene chloride was supplemented, the mixture was washed with 1 N sodium hydroxide solution and then dried over anhydrous magnesium sulfate, the solvent was distilled off. The residue was subjected to silica gel column chromatography and eluted with methylene chloride-methanol-ammonia water (10 : 1 : 0.1). The solvent was distilled off and the resulting colorless crystals were recyrstallized from ethyl acetate to give 0.10 g (37.0%) of N-(2-methyoxyphenyl)-2-methyl -4,5,6,7-tetrahydrobenzimidazole-5-carboxamide monhydrate.

Physicochemical properties:
Melting point: 108°-110° C.

| Elemental analysis (as $C_{16}H_{19}N_3O_2.1.05H_2O$) | | | |
|---|---|---|---|
| | C (%) | H (%) | N (%) |
| Calcd. | 63.16 | 6.98 | 13.81 |
| Found | 62.75 | 6.98 | 13.64 |

Mass spectrum (FAB, Pos):m/z 286 (M++1, as a free base).

REFERENCE EXAMPLE 3

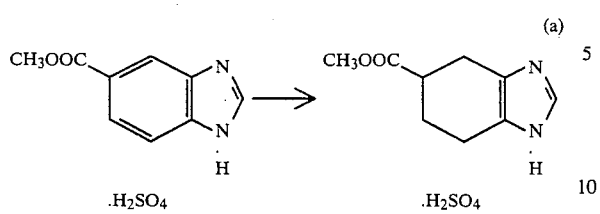

In an autoclave 40.0 g of methyl benzimidazole-5-carboxylate sulfate was dissolved in 600 ml of acetic acid and hydrogenation was carried out at 80° C. for 5 hours under 60 atms using 11 g of 10% palladium carbon as a catalyst. After the catalyst was filtered off, the mother liquor was concentrated under reduced pressure, 41.0 g (yield, 101%) of oily methyl 4,5,6,7-tetrahydrobenzimidazole-5-carboxylate sulfate was obtained.

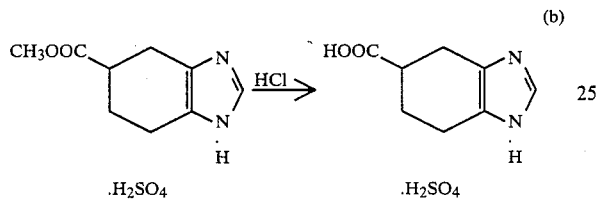

The oily ester sulfate, 41.0 g, described above was dissolved in 350 ml of water and 340 ml of conc. hydrochloric acid followed by stirring at 100° C. for 3 hours. After concentration, the resulting crystals were washed with acetone to give 29.6 g (yield, 76.8% based on the benzimidazole ester) of 4,5,6,7-tetrahydrobenzimidazole-5-carboxylic acid sulfate.

Physicochemical properties:
Melting point: 145°–148° C.
NMR (in d$_6$-DMSO): δ 1.60–3.00 (7H, m), 8.84 (1H, s).
Mass spectrum (EI):m/z 166 (M$^+$, as a free base).
Mass spectrum (CI):m/z 167 (M$^+$+1, as a free base).

REFERENCE EXAMPLE 4

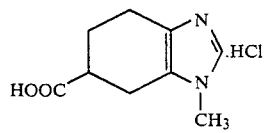

1-Methyl-4,5,6,7-tetrahydrobenzimidazole-6-carboxylic acid hydrochloride

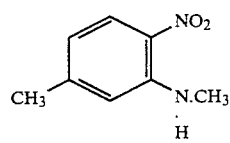

A solution of 9.10 g of 3,4-dinitrotoluene in 100 ml of 30% methylamine/methanol was reacted at 150° C. for 6 hours in a sealed tube. The reaction solution was concentrated under reduced pressure and the residue was subjected to silica gel column chromatography (200 g). Elution with ethyl acetate-hexane (1 : 3) gave 7.95 g (96%) of 3-(N-methylamino)-4-nitrotoluene.

Physicochemical properties:
NMR (CDCl$_3$): δ 2.37 (3H, s), 3,16 (3H, s), 6.30–6.71 (2H, m), 8.00 (1H, d, J=9Hz).

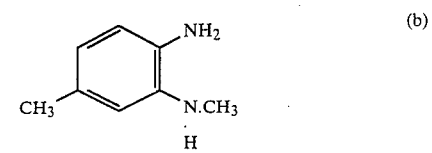

3-(N-Methylamino)-4-nitrotoluene (7.95 g) was catalytically reduced in a solution in 200 ml of methanol using 1.0 g of 10% palladium carbon as a catalyst. After the catalyst was filtered off, the reaction solution was concentrated under reduced pressure to give 6.60 g (101%) of 1-amino-4-methyl-2-(N-methylamino)benzene.

Physicochemical properties:
NMR(CDCl$_3$): δ 2.24(3H, s), 2.82(3H, s), 4.10(3H, br, s), 6.33–6.80(3H, m).

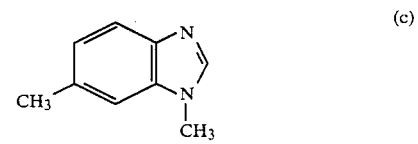

A mixture of 6.60 g of 1-amino-4-methyl-2-(N-methylamino)benzene and a solution of 3.5 ml of formic acid in 50 ml of a 4N HCl was stirred at 100° C. for 3.5 hours. The reaction solution was concentrated under reduced pressure and water was added to the residue. After washing with ethyl acetate, the aqueous phase was rendered alkaline with aqueous potassium carbonate followed by extraction with chloroform. The chloroform layer was washed with saturated sodium chloride solution, dried over anhydrous magnesium sulfate and concentrated under reduced pressure. The residue was subjected to silica gel column chromatography (40 g). Elution with ethyl acetate followed by recyrstallization from ethyl acetate-hexane gave 4.01 g (57%) of 1,6-dimethylbenzimidazole.

Physicochemical properties:
NMR (CDCl$_3$). δ 2.51 (3H, s), 3.76 (3H, s), 7.09 (1H, d, J=8Hz), 7.14 (1H, s), 7.65 (1H, d, J=8Hz), 7.73 (1H, s).

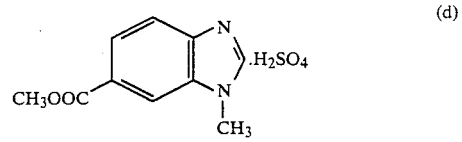

An aqueous solution (100 ml) of 3.95 g of 1,6-dimethylbenzimidazole and 10 g of potassium permanganate was stirred at 50° C. for 2 hours and 2 g of potassium permanganate was further added to the mixture. The mixture was stirred at 80° C. for further 2 hours. After insoluble matters were filtered off, the filtrate was rendered pH 4 with 1 N hydrochloric acid and concentrated under reduced pressure to give 7.33 g of 1- methylbenzimidazole-6-carboxylic acid as the mixture with potassium chloride.

The above compound was heated to reflux in 150 ml of methanol overnight in the presence of 3 ml of conc. sulfuric acid. The reaction solution was concentrated under reduced pressure and water was added to the concentrate. After washing with ethyl acetate, the aqueous layer was rendered alkaline with aqueous potassium carbonate followed by extraction with ethyl acetate. The ethyl acetate layer was washed with saturated aqueous sodium chloride solution, dried over anhydrous magnesium sulfate and concentrated under reduced pressure. The residue was washed with ether to give 2.90 g (56%) of methyl 1-methylbenzimidazole-6-carboxylate.

Physicochemical properties:
NMR (CDCl₃). δ 3.82 (3H, s), 3.91 (3H, s), 7.71 (1H, d,
J=9Hz), 7.84–8.20 (3H, m).

The above compound, 2.80 g, was dissolved in 40 ml of ethanol and 1 ml of conc. sulfuric acid was gradually added dropwise to the solution at room temperature. The resulting crystals were taken by filtration, thoroughly washed with ethanol and dried to give 3.78 g of methyl 1-methylbenzimidazole-6-carboxylate sulfate.

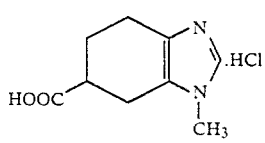

(e)

A solution of 3.39 g of methyl 1-methylbenzimidazole-6-carboxylate sulfate in 70 ml of acetic acid was catalytically hydrogenated at 90° C. for 6 hours under 60 atms using 1.9 g of 5% palladium carbon as a catalyst. Ater the catalyst was filtered off and the reaction solution was concentrated under reduced pressure, ethyl acetate was added to the concentrate followed by extraction with 0.5 N HCl. The aqueous phase was rendered alkaline with potassium carbonate and extracted with chloroform. The chloroform phase was washed with saturated sodium chloride aqueous solution, dried over anhydrous magnesium sulfate and concentrated under reduced pressure to give 2.10 g (92%) of methyl 1-methyl-4,5,6,7-tetrahydrobenzimidazole-6-carboxylate.

The above ester, 2.05 g, was stirred at 100° C. overnight in a solution in 60 ml of 3 N HCl. The reaction solution was concentrated under reduced pressure and the residue was washed with acetone to give 2.19 g (96%) of 1-methyl-4,5,6,7-tetrahydrobenzimidazole-6-carboxylic acid hydrochloride.

Physicochemical properties:
NMR (DMSO-d₆—CD₃OD (1 : 2)): δ 1.70–2.51 (2H, m), 2.57–3.20 (5H, m). 3.82 (3H, s), 8.75 (1H, s).

EXAMPLE 21

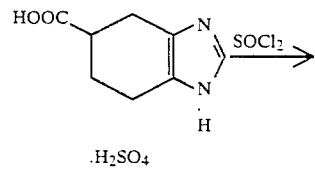

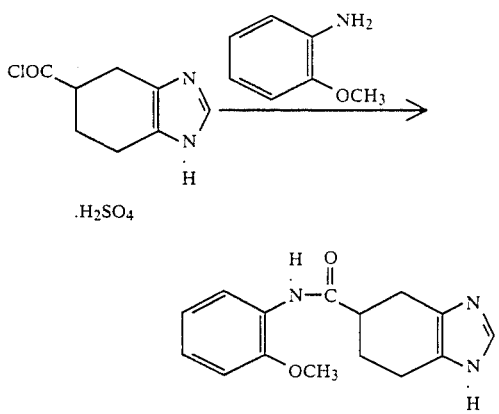

4,5,6,7-Tetrahydrobenzimidazole-5-carboxylic acid sulfate 5.42 g, was stirred in 50 ml of 1,2-dichloroethane and 3 ml of thionyl chloride at 55° to 60° C. for an hour. The solvent was concentrated under reduced pressure and 50 ml of 1,2-dichloroethane was added to the residue, which was again concentrated under reduced pressure. To the reside was added 50 ml of 1,2-dichloroethane. While stirring, 6.25 g of o-anisidine was added dropwise to the mixture below 30° C. After completion of the addition, the mixture was stirred at room temperature for 2 hours and the reaction solution was added to a mixture of 60 ml of water and 30 ml of methanol. After pH was adjusted to about 4.8 with 10% sodium hydroxide solution, the organic phase was separated. To the aqueous phase was added 15 ml of methanol. While stirring under ice cooling, pH was gradually adjusted to 11.0 with 10% sodium hydroxide. The resulting crystals were collected by filtration and washed with a mixture of chilled water -methanol=3 : 1 to give 5.62 g (yield, more than 100%) of N-(2-methoxyphenyl)-4,5,6,7-tetrahydrobenzimidazole-5-carboxamide.

Physicochemical properties:
Melting point: 100°–101.5° C.

| Elemental analysis (as $C_{15}H_{17}N_3O_2.1.5H_2O$) | | | |
|---|---|---|---|
| | C (%) | H (%) | N (%) |
| Calcd. | 60.39 | 6.76 | 14.08 |
| Found | 60.48 | 6.41 | 14.04 |

NMR (CDCl₃-DMSO-d₆): δ 1.80–240 (m, 2H), 2.52–3.04 (m, 5H), 3.90 (s, 3H), 6.8–7.12 (m, 3H), 7.40 (s, 1H), 8.12–8.28 (dd, 1H), 8.30 (brds, 1H). Mass spectrum (EI):m/z 271 (M³⁰).

EXAMPLE 22

N-(2-Methoxyphenyl)-4,5,6,7-tetrahydrobenzimidazole-5-carboxamide, 5.07 g, obtained in Example 21 was treated with ethanol-hydrochloric acid in ethanol to give 5.66 g (yield 98.4%) of N-(2-methoxyphenyl) -4,5,6,7-tetrahydrobenzimidazole-5-carboxamide hydrochloride.

Physicochemical properties:
Melting point: >250° C.

| Elemental analysis (as $C_{15}H_{17}N_3O_2.HCl$) | | | | |
|---|---|---|---|---|
| | C (%) | H (%) | N (%) | Cl (%) |
| Calcd. | 58.54 | 5.89 | 13.65 | 11.52 |

-continued

| Elemental analysis (as $C_{15}H_{17}N_3O_2.HCl$) | | | | |
|---|---|---|---|---|
| | C (%) | H (%) | N (%) | Cl (%) |
| Found | 58.24 | 5.98 | 13.48 | 11.68 |

Mass spectrum (EI):m/z 271 (M+, as a free base).

EXAMPLE 23

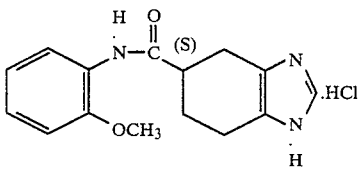

(S)-(−)-N-(2-Methoxyphenyl)-4,5,6,7-tetrahimidazole-5-carboxamide hydrochloride (a) (±)-N-(2-methoxyphenyl)-4,5,6,7-tetrahydrobenzimidazole-5-carboxamide, 5.0 g, obtained in Example 21 was dissolved in 70 ml of methanol and a solution of 3.47 g of (−)-dibenzoyl tartaric acid in 300ml of methanol was added to the solution. The resulting crystals were taken by filtration. The crystals were recrystallized twice from dimethylformamide and water to give 1.89 g of (S)-(−)-N-(2-methoxyphenyl)-4,5,6,7-tetrahydrobenzimidazole-5-carboxamide (−) dibenzoyl tartarate showing a rotation of -55.9° (20° C., sodium D line, c=1.02 g/dl, dimethylformamide).
Physicochemical properties:
Melting point: 142.0°-143.5° C.

| Elemental analysis (as $C_{15}H_{17}N_3O_2.C_{18}H_{14}O_8.1.2H_2O$) | | | |
|---|---|---|---|
| | C (%) | H (%) | N (%) |
| Calcd. | 60.86 | 5.17 | 6.45 |
| Found | 60.86 | 5.17 | 6.61 |

Mass spectrum (EI):m/z 271 (M+, as a free base). (b) The above-mentioned tartarate, 1.70 g, was added to 2N hydrochloric acid. After washing with ethyl acetate, sodium carbonate was added to the phase to render pH about 9. The aqueous phase was extracted with chloroform-methanol (4 : 1). After the extract was dried over anhydrous magnesium sulfate, the solvent was distilled off. Recrystallization of 0.15 g of the resulting foamy substance from ethanol-water gave 0.1 g of (S)-(−)-N-(2-methoxyphenyl)-4,5,6,7-tetrahydrobenzimidozole-5-carboxamide showing a rotation of −27.0° (20° C., sodium D line, C=1.08 g/dl, methanol) as crystals.
Physicochemical properties:
Melting point: 99.5°-100.5° C.

| Elemental analysis (as $C_{15}H_{17}N_3O_2.H_2O$) | | | |
|---|---|---|---|
| | C (%) | H (%) | N (%) |
| Calcd. | 62.27 | 6.62 | 14.52 |
| Found | 62.33 | 6.67 | 14.55 |

Mass spectrum (EI):m/z 271 (M30 ). (c) The compound obtained above was dissolved in ethanol-ethyl acetate and the solution was treated with a hydrogen chloride-ethyl acetate solution to give 0.49 g of (S)-(−)-N-(2-methoxyphenyl)-4,5,6,7-tetrahydrobenzimidazole-5-carboxamide hydrochloride showing a rotation of −12.2° (20° C., sodium D line, C=1.08 g/dl, methanol) as crystals.
Physicochemical properties:
Melting Point: 215°-222° C. (decomposition).

| Elemental analysis (as $C_{15}H_{17}N_3O_2.HCl.0.5H_2O$) | | | |
|---|---|---|---|
| | C (%) | H (%) | N (%) |
| Calcd. | 56.87 | 6.05 | 13.26 |
| Found | 56.77 | 6.01 | 13.24 |

Mass spectrum (EI):m/z 271 (M+, as a free base)

EXAMPLE 24

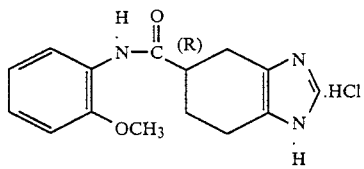

(R)-(+)-N-(2-Methoxyphenyl)-4,5,6,7-tetrahydrobenzimidazole-5-carboxamide hydrochloride (a) (R)-(+)-N-(2-Methoxyphenyl)-4,5,6,7-tetrahydrobenzimidazole-5-carboxamide (+)-dibenzoyl tartarate showing a rotation of +56.1° (20° C., sodium D line, c=1.03 g/dl, dimethylformamide) was obtained as crystals using (+)-dibenzoyl tartaric acid in a similar manner to

EXAMPLE 23 (a).

Physicochemical properties:
Melting point: 139.0°-141.0° C.

| Elemental analysis (as $C_{15}H_{17}N_3O_2.C_{18}H_{14}O_8.1.1H_2O$) | | | |
|---|---|---|---|
| | C (%) | H (%) | N (%) |
| Calcd. | 61.03 | 5.15 | 6.47 |
| Found | 60.99 | 5.11 | 6.57 |

Mass spectrum (EI):m/z 271 (M+, as a free base).
(b) (R)-(+)-N-(2-Methoxyphenyl)-4,5,6,7-tetrahydrobenzimidazole-5-carboxamide showing a rotation of +27.4° (20° C., sodium D line, c=1.04 g/dl, methanol) was obtained as crystals from the tartarate obtained in (a) in asimilar manner to Example 23 (b).
Physicochemical properties
Melting point: 100.0°-101.0° C.

| Elemental analysis (as $C_{15}H_{17}N_3O_2.H_2O$) | | | |
|---|---|---|---|
| | C (%) | H (%) | N (%) |
| Calcd. | 62.27 | 6.62 | 14.52 |
| Found | 62.07 | 6.65 | 14.51 |

Mass spectrum (EI)L:m/z 271 (M+).
(c) (R)-(+)-N-(2-Methoxyphenyl)-4,5,6,7-tetrahydrobenzimidazole-5-carboxamide hydrochloride showing a rotation of +12.3° (20° C., sodium D line, c=1.09 g/dl, methanol) was obtained as crystals from the compound obtained in (b) in a similar manner to Example 23 (c).
Physicochemical properties:
Melting point: 217°-223° C.

| Elemental analysis (as $C_{15}H_{17}N_3O_2 \cdot HCl$) | | | |
|---|---|---|---|
| | C (%) | H (%) | N (%) |
| Calcd. | 58.54 | 6.01 | 13.24 |
| Found | 58.54 | 5.93 | 13.59 |

Mass spectrum (EI):m/z 217 (M+, as a free base).

The following compounds were prepared in a similar manner to Example 21.

EXAMPLE 25

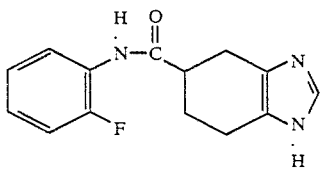

N-(2-Fluorophenyl)-4,5,6,7-tetrahydrobenzimidazole-5-carboxamide

Physicochemical properties:
Melting point: 164°–165° C.

| Elemental analysis (as $C_{14}H_{14}N_3OF \cdot H_2O$) | | | | |
|---|---|---|---|---|
| | C (%) | H (%) | N (%) | F (%) |
| Calcd. | 60.64 | 5.82 | 15.15 | 6.85 |
| Found | 60.82 | 5.79 | 15.18 | 6.83 |

Mass spectrum (EI):m/z 259 (M+).

EXAMPLE 26

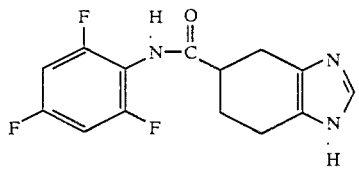

N-)2,4,6-Trifluorophenyl)-4,5,6,7-tetrahydrobenzimidazole-5carboxamide

Physicochemical properties:
Melting point: 223°–224° C.

| Elemental analysis (as $C_{14}H_{12}N_3OF_3 \cdot 0.4H_2O$) | | | | |
|---|---|---|---|---|
| | C (%) | H (%) | N (%) | F (%) |
| Calcd. | 55.59 | 4.27 | 13.89 | 18.84 |
| Found | 55.53 | 4.43 | 13.84 | 18.75 |

Mass spectrum (EI):m/z: 295 (M+).

EXAMPLE 27

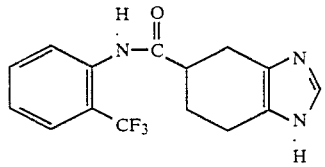

N-(2-Trifluoromethylphenyl)-4,5,6,7-tetrahydrobenzimidazole-5-carboxamide

Physicochemical properties:
Melting point: 222°–223° C.

| Elemental analysis (as $C_{15}H_{14}N_3OF_3 \cdot 0.5H_2O$) | | | | |
|---|---|---|---|---|
| | C (%) | H (%) | N (%) | F (%) |
| Calcd. | 56.60 | 4.75 | 13.20 | 17.90 |
| Found | 56.51 | 4.74 | 13.16 | 17.13 |

Mass spectrum (EI):m/z 309 (M+)

EXAMPLE 28

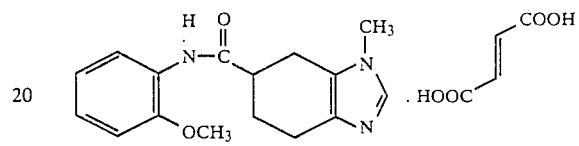

1-Methyl-4,5,6,7-tetrahydrobenzimidazole -6carboxylate hydrochloride obtained in Reference Example 4 was treated in a similar manner to Example 21 and further converted into the fumarate in a known method to give N-(2-methoxyphenyl) -1methyl-4,5,6,7-tetrahydrobenzimidazole -6-carboxamide fumarate.

Physicochemical properties:
Melting point: 188°–190° C. (methanol-acetonitrile).

| Elemental analysis (as $C_{16}H_{19}N_3O_2 \cdot C_4H_4O_4 \cdot H_2O$) | | | |
|---|---|---|---|
| | C (%) | H (%) | N (%) |
| Calcd. | 57.27 | 6.01 | 10.02 |
| Found | 57.56 | 5.56 | 10.12 |

Mass spectrum (EI):m/z 285 (M+, as a free base).
NMR (DMSO-$d_6$): δ 1.48–2.16 (2H, m), 2.34–3.13 (5H, m), 3.50 (3H, s), 3.79 (3H, s), 6.56 (2H, s), 6.72–7.13 (3H, m), 7.68 (1H, s), 7.88 (1H, d, J=8Hz), 9.16 (1H, s).

We claim:

1. A 4,5,6,7-tetrahydrobenzimidazole derivative represented by general formula (I):

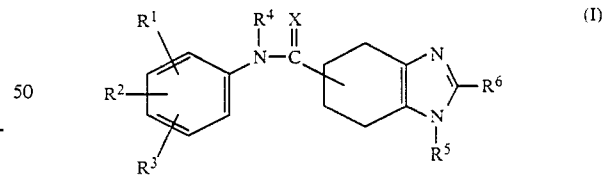

(wherein $R^1$, $R^2$ and $R^3$ independently represent hydrogen atom, hydroxy group, a halogen atom, a lower alkyl group which may optionally be substituted with a halogen atom, a lower alkoxy group, a lower alkylthio group, an aralkyloxy group, an aryloxy group, a lower alkanoyl group, carboxy group, a lower alkoxycarbonyl group or nitro group; $R^4$, $R^5$ and $R^6$ independently represent hydrogen atom or a lower alkyl group; and X represents oxygen atom or sulfur atom), or a tautomer thereof or a pharmceutically acceptable salt thereof.

2. A compound represented by general formula (I) as claimed in claim 1, wherein $R^1$, $R^2$ and $R^3$ independently represent hydrogen atom or a lower alkoxy group.

3. A compound of claim 2, which is N-(2-methoxyphenyl)-4,5,6,7-tetrahydrobenzimidazole -5-carboxamide.

4. A compound of claim 2, which is N-(2-ethoxyphenyl)-4,5,6,7-tetrahydrobenzimidazole-5-carboxamide.

5. A pharmaceutical composition useful as a 5-HT$_3$ antagonist comprising an effective amount of 4,5,6,7-tetrahydrobenzimidazole derivative represented by formula (I):

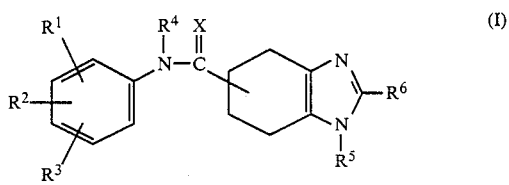

wherein $R^1$, $R^2$ and $R^3$ independently represent hydrogen atom, hydroxy group, a halogen atom, a lower alkyl group which may optonally be substituted with a halogen atom, a lower alkoxy group, a lower alkylthio group, an aralkyloxy group, an aryloxy group, a lower alkanoyl group, carboxy group, a lower alkoxycarbonyl group or nitro group; $R^4$, $R^5$ and $R^6$ independently represent hydrogen atom or a lower alkyl group; and X represens oxygen atom or sulfur atom, or a tautomer thereof or a pharmaceutically acceptable salt thereof and a pharmaceutically acceptable carrier.

6. A pharmaceutical composition of claim 5, which is a drug for treating gastrointestinal disorders.

7. A pharmaceutical composition of claim 6, wherein said gastrointestinal disorders are initable bowel syndrome.

8. A pharmaceutical composition of claim 5, which is a drug for treating nausea and/or vomiting induced by chemotherapy or radiations.

9. A pharmaceutical composition of claim 5, which is a drug for treating migraine, cluster headache and trigeminal neuralgia.

10. A pharmaceutical composition of claim 5 which is a drug for treatng anxiety and psychosis. wherein said gastrointestinal disorders are initable bowel.

* * * * *